United States Patent
Fowler et al.

(10) Patent No.: US 12,350,462 B1
(45) Date of Patent: Jul. 8, 2025

(54) SMOKE SUCTION FLOW REGULATOR

(71) Applicant: Northgate Technologies Inc., Elgin, IL (US)

(72) Inventors: Paul Fowler, Belvidere, IL (US); Alexander Carlo Buscaglia, Franklin, IN (US); Ju-Hyoung Kim, Naperville, IL (US)

(73) Assignee: NORTHGATE TECHNOLOGIES, INC., Elgin, IL (US)

(*) Notice: Subject to any disclaimer, the term of this patent is extended or adjusted under 35 U.S.C. 154(b) by 853 days.

(21) Appl. No.: 17/518,372

(22) Filed: Nov. 3, 2021

Related U.S. Application Data (60) Provisional application No. 63/109,696, filed on Nov. 4, 2020.

(51) Int. Cl.
```
A61M 39/22     (2006.01)
A61B 17/00     (2006.01)
A61B 17/34     (2006.01)
A61M 13/00     (2006.01)
A61M 39/10     (2006.01)
```

(52) U.S. Cl.
CPC ....... *A61M 39/22* (2013.01); *A61B 17/00234* (2013.01); *A61B 17/3474* (2013.01); *A61M 13/006* (2014.02); *A61M 2039/1038* (2013.01); *A61M 2205/3331* (2013.01); *A61M 2205/582* (2013.01)

(58) Field of Classification Search
CPC ................ A61M 39/22; A61M 13/006; A61M 2039/1038; A61M 2205/3331; A61M 2205/582; A61M 5/16881; A61M 16/20; A61M 2039/2486; A61M 39/283; A61B 17/00234; A61B 17/3474
See application file for complete search history.

(56) References Cited

U.S. PATENT DOCUMENTS

| | | | | |
|---|---|---|---|---|
| 3,332,439 A * | 7/1967 | Burke | ........... | A61M 39/283 |
| | | | | D24/129 |
| 3,841,354 A * | 10/1974 | McDonnell | ....... | A61M 5/16881 |
| | | | | D24/129 |
| 6,090,094 A * | 7/2000 | Clifford, Jr. | ........... | A61M 39/22 |
| | | | | 604/28 |
| 8,029,493 B2 * | 10/2011 | Asfora | ..................... | A61M 1/82 |
| | | | | 604/506 |
| 8,931,760 B2 * | 1/2015 | Ikeda | ..................... | F16K 5/0689 |
| | | | | 251/192 |
| 2017/0067568 A1* | 3/2017 | Duncan | ............... | F16K 11/0853 |
| 2020/0222683 A1* | 7/2020 | Doll | ....................... | A61M 39/22 |

* cited by examiner

*Primary Examiner* — Theodore J Stigell
(74) *Attorney, Agent, or Firm* — Crowell & Moring LLP (57) ABSTRACT

A smoke evacuation flow regulator for use with a suction source to rapidly remove excess smoke during an endoscopic surgical procedure is described. The smoke evacuation regulator may include a body having a gas pathway and a knob assembly threadably attached to the body that is sized to completely open or completely close the gas pathway in a single revolution of the knob assembly. The head of the knob assembly may be sized and shaped to permit tactile determination of the rotational position of the knob assembly in low vision situations. The body of the smoke evacuation flow regulator may include a knob assembly retaining arm that cooperates with a disk or extension on the knob assembly to allow rotational freedom of the knob assembly, but prevent inadvertent removal of the knob assembly from the body during use.

20 Claims, 7 Drawing Sheets

SMOKE SUCTION FLOW REGULATOR

CROSS-REFERENCE TO RELATED APPLICATIONS

This application claims the benefit of U.S. Provisional Patent App. No. 63/109,696, filed Nov. 4, 2020, the entirety of which is hereby incorporated herein by reference.

BACKGROUND

1. Technical Field Text

The present disclosure relates to a flow regulator for smoke suction for use in gas recirculation systems used in minimally invasive surgical procedures.

2. Background Information

Minimally invasive surgical procedures, including endoscopic surgical procedures, such as laparoscopic, arthroscopic, hyteroscopic, thoracoscopic surgical procedures, are becoming more common place in the surgical environment due to shorter recovery times, shorter operating durations, and reduced costs. Minimally invasive surgical procedures are typically performed with instruments inserted through small, artificially created openings or portals in the patient.

In a laparoscopic surgical procedure, a gas is injected into the peritoneal cavity through an artificial opening in the abdomen created by a verres needle. Typically, the type of gas that is injected is a $CO_2$ gas, although a mixture of two or more gases or a different gas may also be suitable depending on the surgical procedure. In a laparoscopic procedure, the $CO_2$ gas is used to distend the pneumoperitoneum, thereby creating an air space for the surgeon to visualize the organs and to maneuver surgical instruments and an endoscope. The $CO_2$ gas is injected into the peritoneal cavity under pressure by an insufflation device.

After the pneumoperitoneum is first distended, an endoscope with a camera (which is connected to a monitor) is inserted into the abdominal cavity to visualize the interior of the cavity and, more particularly, the operative space. The endoscope typically remains inserted for the duration of the surgical procedure. Other openings may also be created to provide access to other surgical instruments into the abdominal cavity.

The instrumentation used to cut, cauterize, ablate or vaporize tissues inside the abdomen during a minimally invasive surgical procedure, such as a laparoscopic procedure, typically generates surgical smoke. This surgical smoke may pose a health risk to the patient and may also pose a health risk to the surgeon and other individuals in the operating room if some or all of the surgical smoke escapes to the operating room. As used herein, the term "surgical smoke" includes, without limitation, gases or aerosols that may contain toxins, particulate matter, irritants, viable cells and viruses, water vapor, and other contaminants. Surgical smoke also impairs the surgeon's visualization via the camera in the endoscope. This impairment to visualization can also be further accentuated by fogging or condensation on the camera lens due to the $CO_2$ gas entering the abdominal cavity at below body temperature. Impairing visualization can interfere with the surgical procedure and result in risk to the patient's health. Furthermore, impairing visualization may also lead to delays in the operation, in particular in operations involving robotic assisted surgical procedures performed remotely.

Procedures that generate surgical smoke generally require a negative pressure (vacuum) system along with a connection to the patient to achieve smoke evacuation/gas suction if clinically applicable. This clears the vision field during surgery and allows the surgeon to better perform the procedures/activities that require direct visualization (through the use of a scope inserted via a trocar). A typical connection to the patient is a tubing set that links the negative pressure system to a trocar that extends into the pneumoperitoneum. A problem with these evacuation systems is that the negative pressure can sometimes exceed the ability of the insufflator to inject gas and maintain the pneumoperitoneum. This would result in a collapse of the pneumoperitoneum if the vacuum system is turned on.

DETAILED DESCRIPTION

The present disclosure is directed to a smoke evacuation flow regulator (also referred to herein as the smoke suction flow regulator or smoke suction valve) that may allow for improved visualization and performance over existing smoke evacuation control mechanisms used in gas recirculation systems.

A current solution for removing surgical smoke is through the use of a simple on/off valve applied inline to the smoke evacuation tubing set. The current solution of an on/off valve allows for gross control of the negative pressure applied (all on, or all off). Surgeries that use this type of tubing set now will typically either turn the valve on for a short period of time and then turn it off, or will try to "partially" turn the valve on by acutely aligning the on/off valve so that only a portion of the through hole is "on". This does not provide enough variability to the flow that is needed during surgery and is also prone to inconsistency and potential surgical issues if the valve is bumped or erroneously adjusted. A smoke suction flow regulator that allows for more control of the flow, such as a gradual increase from closed to open, and consistency for repeatability between procedures, is described herein.

Another issue related to controlling smoke evacuation that presents itself in a surgical setting is the ability to determine the setting of a smoke evacuation valve in the dim lighting of an operating room, or without direct visualization to the smoke evacuation valve at all. Smoke evacuation valves currently used may require directly visualizing the setting to have it correctly adjusted. Without direct visualization, the operating room staff will typically adjust the smoke evacuation valve by looking at the insufflator to see if it can keep up with the gas evacuation and/or asking the surgeon if the smoke evacuation is adequate. The smoke evacuation regulator described herein provides a way of determining the flow without seeing the valve, and an ability to set the valve to a predetermined setting based on previous use/history.

As shown and described herein, an improved smoke evacuation regulator, according to one implementation, allows for variable and gradual flow (through the use of a specific thread pitch and size) with a consistent and high negative pressure. A user of the valve may determine a setting of the disclosed smoke evacuation regulator through external ridges and an indicator as shown. Also, in one embodiment, the smoke evacuation regulator may be assembled in a manner that permanently locks the threaded knob of the controller to the base through the use of a retention/snap feature while allowing for variable flow settings. In alternative implementations a filter may be directly embedded into the flow control valve for added filtration in the device to be used with any various application, rather than an inline filter that requires a specific assembly.

Although any of a number of biocompatible materials are contemplated for use in the smoke evacuation regulator described herein, biocompatible plastics such as natural colored HIPS and blue makrolon (polycarbonate) may be used in one implementation. The smoke evacuation regulator may be formed using an injection molding technique and assembled as a two-component assembly in one implementation.

As best seen in FIGS. 1A-1C and 2A-2C, the smoke evacuation regulator (also referred to herein as a suction flow regulator or a smoke evacuation valve) 100 may be constructed with a two piece assembly consisting of 1) a base 102 that contains the gas path 104 and retention feature 106 for the knob, and 2) a threaded knob 108 with a threaded region 109, where the threaded knob 108 includes a protruding member 110, to close off the gas path 104 if the knob is threaded all the way into the base 102, and a "locking" disk 112 that interacts with the base to be able to snap into the retention features 106. The top surface 113 of the threaded knob 108 may have a helical surface topography that includes numbers 117 to assist with communicating the flow setting of the suction flow regulator 100. For the setting indication, the threaded knob 108 (See also FIGS. 3A-3F) includes raised ridges 114 that are numerically grouped and spaced around the side gripping region of the knob adjacent/perpendicular to the setting numbers 117 on the top surface 113 to indicate the numerical setting/magnitude of gas flow.

The raised ridges 114 may work with an indicator member 116 formed in the molded base 102 (See also FIGS. 4A-4E), where the indicator member 116 may be an arrow that aligns with the threaded knob and indicates which setting the knob 108 is in (and thus indicating how much of the gas passage 104 in the base 102 is being blocked by the protruding member 110 on the end of the knob 108). The gas passage 104 may terminate in opposing openings that each have barbs 117 around the outer diameter of the gas passage for tubing attachment. Also, the openings at the ends of the gas passage 104 may define an orifice sized to allow greater than 10 liter per minute of gas flow (e.g. $CO_2$ gas) with approximately 480 mmHG vacuum pressure.

For the setting indication and gradual flow of the gas evacuation, a specific thread size that corresponds with the gas flow path 104 to allow for one full revolution of the knob 108 from completely open to completely closed is contemplated. For example, a ⅝-11 thread may be used that causes movement up or down of 0.91 inch with every revolution of the knob 108. The 0.91 inch movement would work well with a gas flow path orifice of 0.90 inches that supports >10 LPM flow of carbon dioxide gas ($CO_2$) and an approximately 480 mmHG (millimeters of mercury) vacuum. This thread size/gas flow path ID relationship may be scaled both larger and smaller depending on the indication, but would preferably be sized such that one full rotation of the threaded knob would allow for complete translation across the inner diameter (ID) cross-section of the gas flow path 104 in the base from fully open to fully closed. In other embodiments, a threading angle/pitch of the knob 108 and the body 102 may be designed such that rotation of the threaded knob 108 to fully open or close the gas pathway 104 on the base 102 over more than one full rotation, for example 1.5 or 2 full revolutions of the knob 108, may be implemented.

For a retention feature 106 that prevents the knob 108 from being inadvertently completely detached from the base, the base component of the two-piece assembly may contain one or more protruding arms 118 with an overhang 120 having a smaller ID than the disk 112 located on the threaded knob 108. The protruding arms 118 are flexible or movable to allow for the threaded knob 108 to insert into the base 102 but prevent backout/disassembly. Thus, in one embodiment, the protruding arms 118 may be made of a thickness and material to flex when the knob 108 is inserted and then resiliently snaps back to a default unflexed position that captures the disk 112 above the start of the threads, and underneath the gripping region, of the knob 108. The protruding arms 118 may include ribs 119 for grip and snap reinforcement. The amount of movement of the knob 108 perpendicular and away from the gas flow path 104 of the base 102 may then be limited by the protruding arms 118 without interfering with the rotational motion of the knob, as shown in the sequence of FIGS. 2A-2C.

Figure 1A:
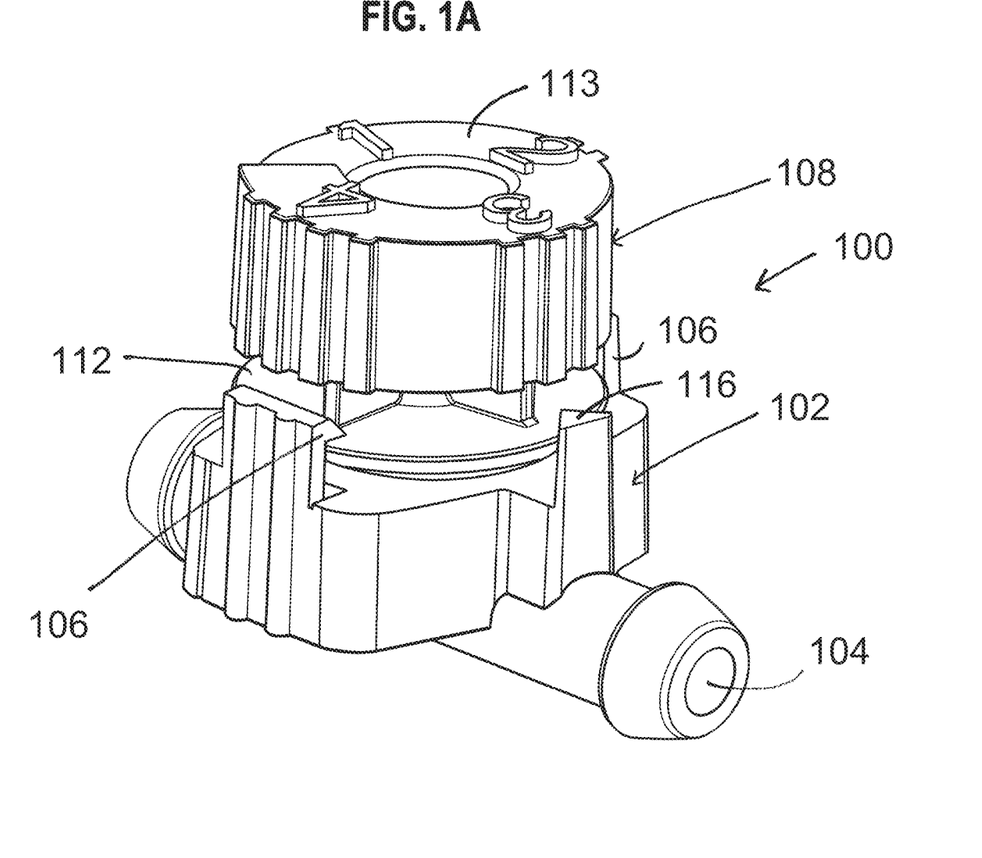
FIG. 1A is a perspective view of an embodiment of smoke suction flow regulator system that may be used with an insufflator or other gas recirculation system.
Figure 1B:
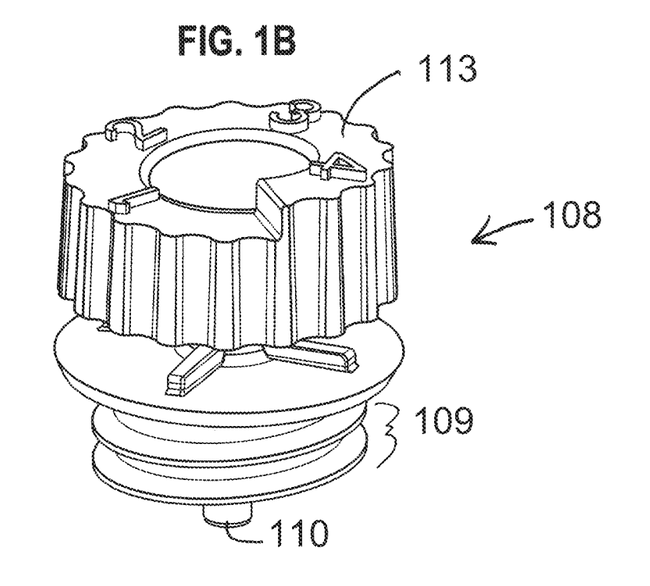
FIG. 1B is a perspective view of the base of the smoke suction flow regulator of FIG. 1A.
Figure 1C:
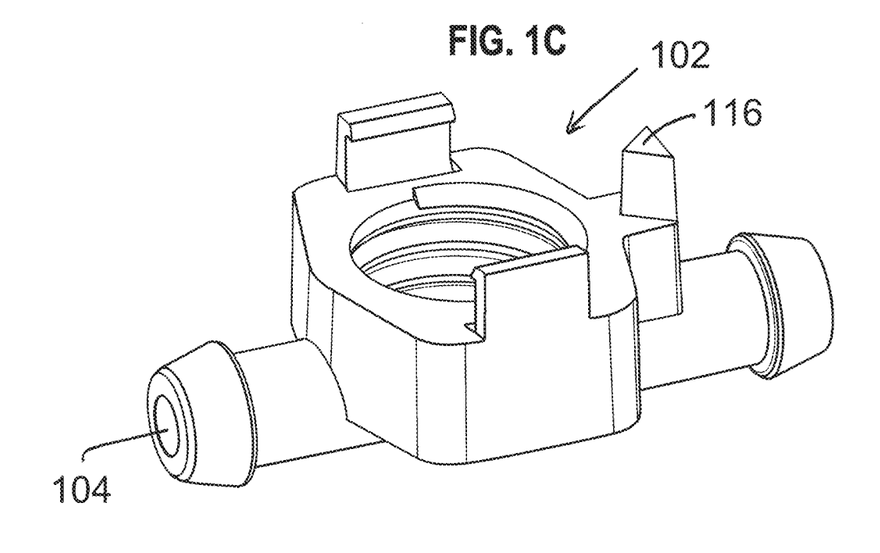
FIG. 1C is a perspective view of the knob assembly of the smoke suction flow regulator of FIG. 1A.
Figure 2A:
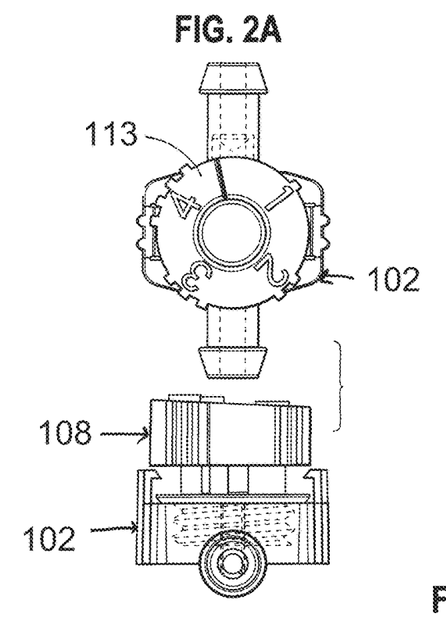
FIG. 2A is a top and end view of the smoke suction flow regulator of FIG. 1A showing the knob assembly at a first setting that fully blocks a flow path through the smoke suction flow regulator.
Figure 2B:
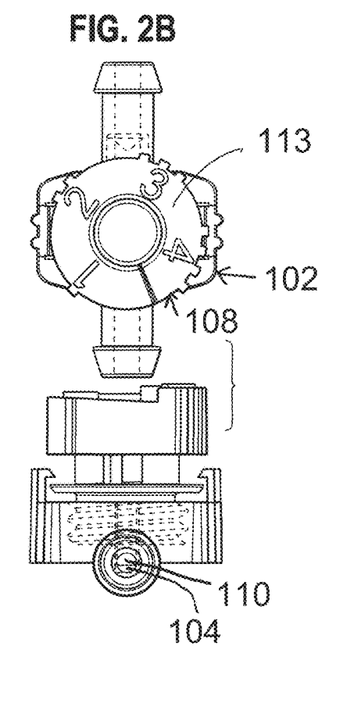
FIG. 2B is a top and end view of the smoke suction flow regulator of FIG. 1A showing the knob assembly at a second setting where the flow path through the smoke suction flow regulator is approximately half blocked.
Figure 2C:
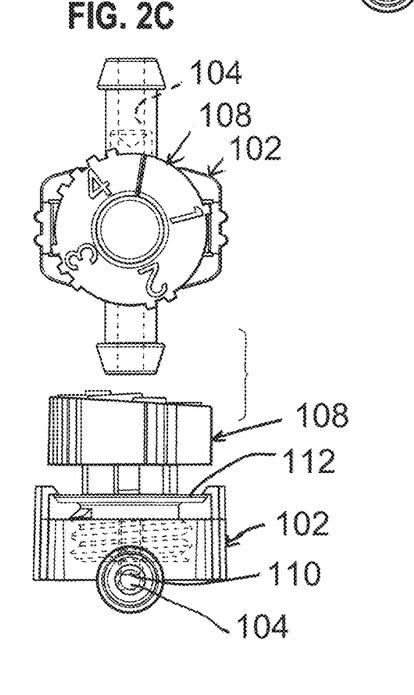
FIG. 2C is a top and end view of the smoke suction flow regulator of FIG. 1A showing the knob assembly at a third setting where the flow path through the smoke suction flow regulator is substantially unblocked.
Figure 3A:
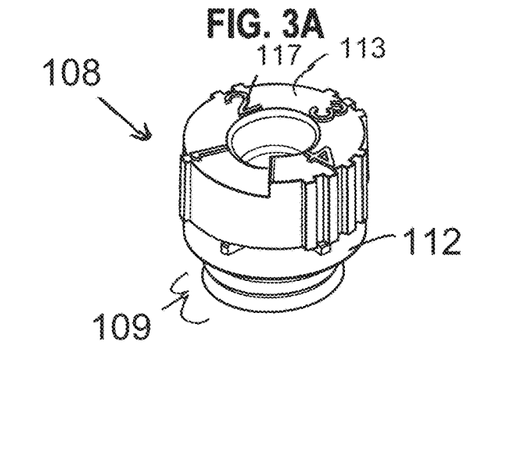
FIGS. 3A-3F are different views and cross sections of the knob assembly of FIG. 1B.
Figure 3B:
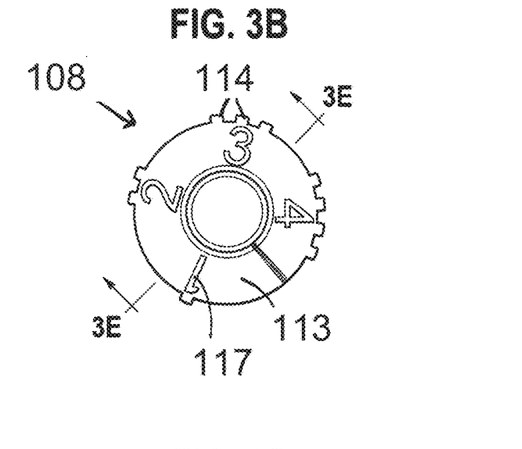
Figure 3C:
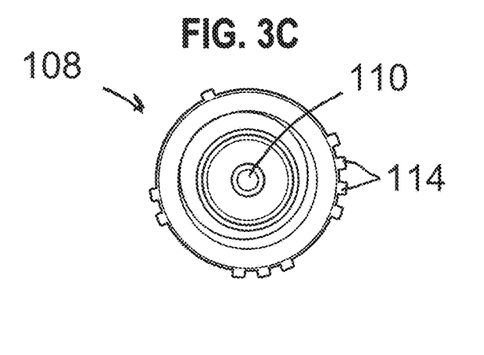
Figure 3D:
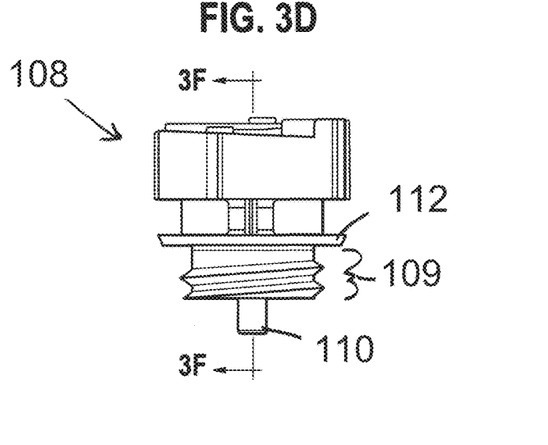
Figure 3E:
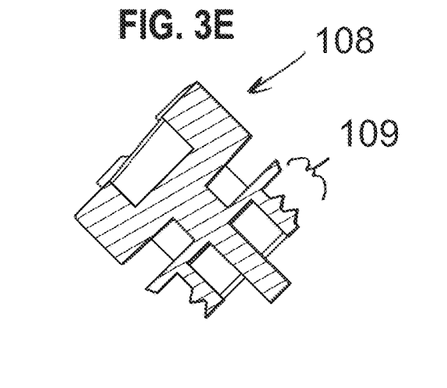
Figure 3F:
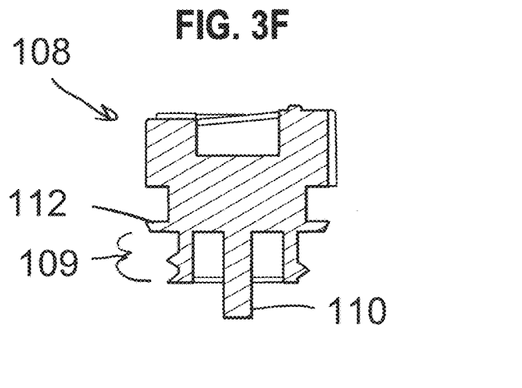
Figure 4A:
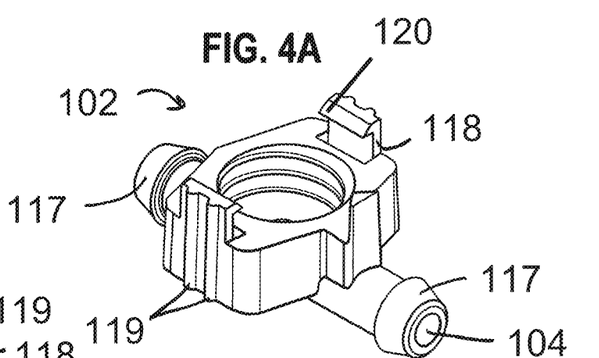
FIGS. 4A-4E are different views and cross sections of the smoke suction flow regulator base of FIG. 1C.
Figure 4B:
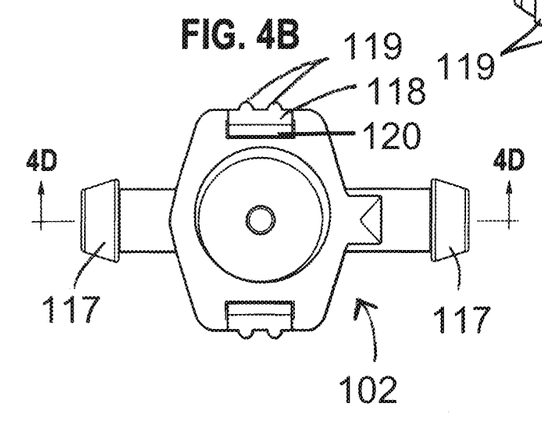
Figure 4C:
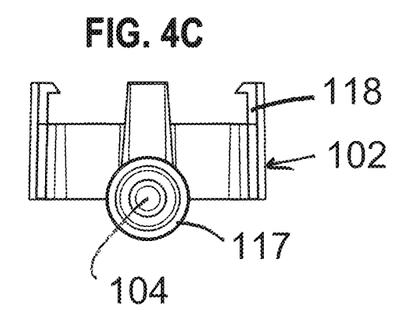
Figure 4D:
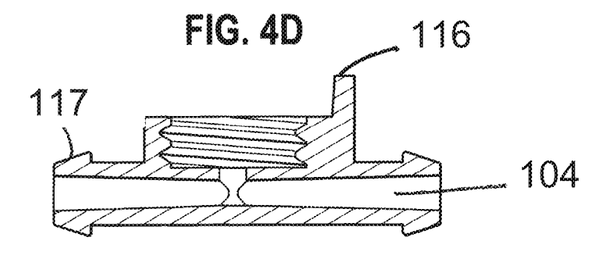
Figure 4E:
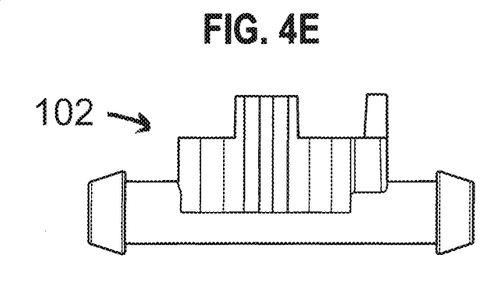

Referring to FIGS. 2A-2C, the progression of travel of the blocking portion 110 per revolution of the threaded knob 108 is illustrated, for example when the threads on the threaded knob are ⅝-11 threads. FIG. 2A shows the regulator 100 at a setting of less than 1 where the gas pathway is fully blocked by the blocking portion. FIG. 2B shows a setting of approximately 3 where the gas pathway is about one half obstructed. FIG. 2C shows the setting at greater than 4 where the gas pathway is almost entirely unblocked.

Figure 5:
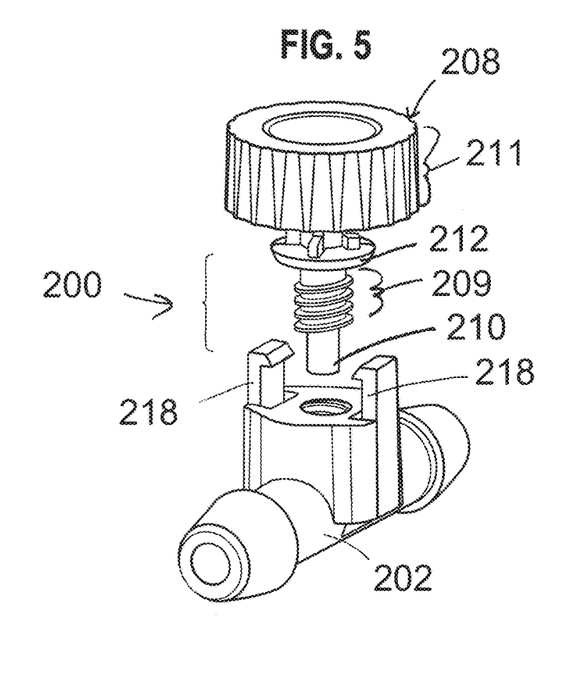
FIG. 5 is a first alternative embodiment of the smoke suction flow regulator of FIG. 1A.
Figure 6:
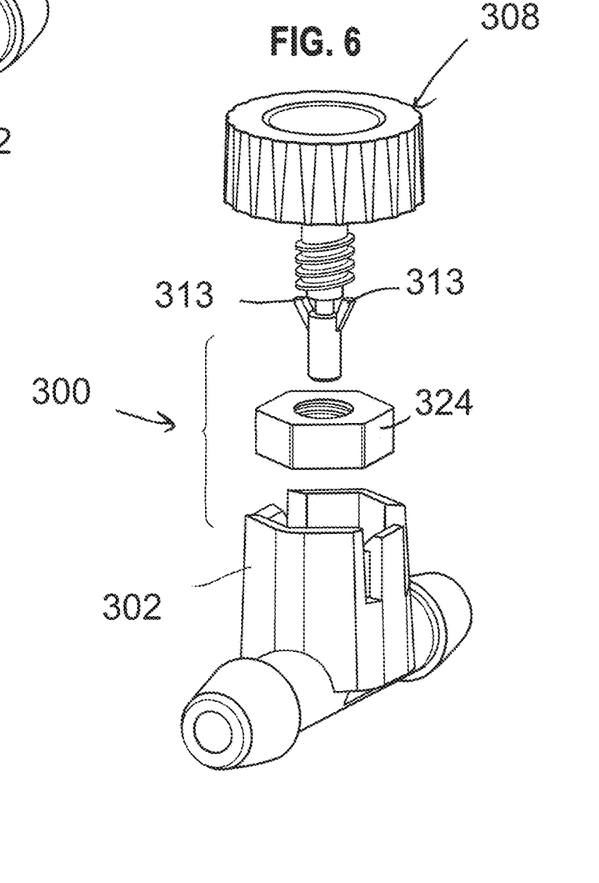
FIG. 6 is a second alternative embodiment of the smoke suction flow regulator of FIG. 1A.

FIGS. 5 and 6 illustrate alternative embodiments of a suction flow regulator 200, 300. FIG. 5. includes a suction flow regulator 200 with a threaded knob 208 positionable in a base 202 in much the same manner as the embodiment of FIGS. 1-4. The threaded knob 208 of FIG. 5, however, has a narrower diameter threaded region 209 and smaller diameter retention disk 212 above the threaded portion and below the knob gripping region 211 than the embodiment of FIGS. 1-4. The protruding arms 218 from the base 202 are similarly scaled down in their spacing to work with reduced diameter retention disk 212. The alternative embodiment of a suction flow regulator 300 shown in FIG. 6 incorporates a different retention mechanism, where a hexagonal-shaped nut 324 frictionally fits into a complementary hexagonal-shaped cradle or recessed area on the base portion 302 that receives the nut 324. The knob assembly 308 in FIG. 6 then includes a pair of flexible retaining barbs 313 biased outward from the shaft of the knob assembly, and that retract into or toward the shaft of the knob assembly when inserted into the nut. The retaining barbs 313 then snap back out to their default outward position after they pass through the nut 324 such that they will catch on the underside of the nut to stop vertical motion and removal of the knob assembly 308 when the knob assembly is unscrewed or pulled back out too far.

Figure 7:
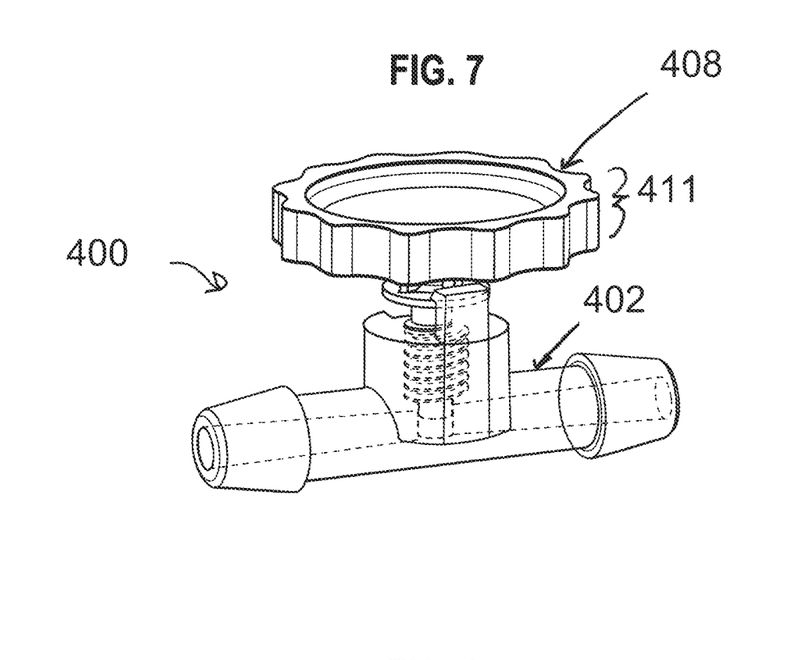
FIG. 7 illustrates a perspective view of a first alternative embodiment of the smoke suction flow regulator of FIG. 5.
Figure 8:
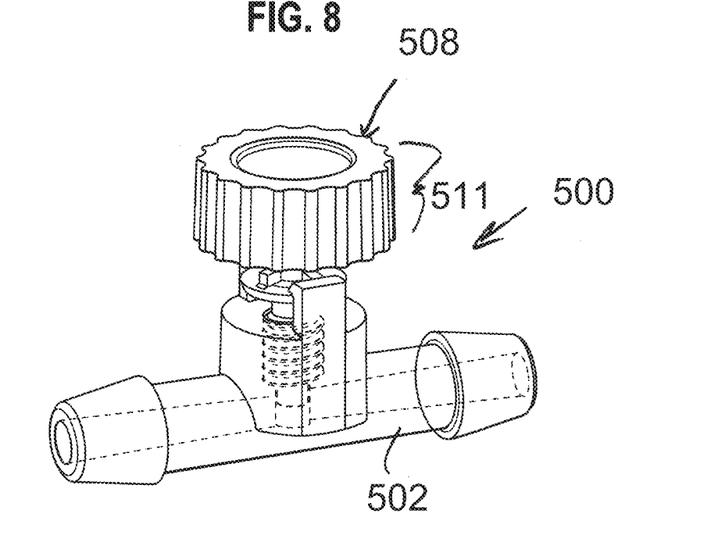
FIG. 8 illustrates a perspective view of a second alternative embodiment of the smoke suction flow regulator of FIG. 5.

Different embodiments of the gripping region 411, 511 (proximal end of the knob assembly) of the knob 408, 508 are shown in FIGS. 7 and 8. A smoke evacuation valve 400, with a knob 408 having a wide diameter, but a relatively thin depth, gripping region 411 is shown in FIG. 7, and a smoke evacuation valve 500 with a narrower diameter knob 508 but a thicker proportional depth for the gripping region 511 than the version of FIG. 7 is shown in FIG. 8. In another alternative embodiment, a filtration media may be included, either included in the two-piece design, or as a three-piece design with a filter body/housing combined when the pieces are molded.

The smoke suction flow regulator may, in one embodiment, be connected to a gas recirculation system via a valve that branches off of the closed recirculation pathway of the gas recirculation system, where the valve between the closed recirculation path and the suction exhaust path containing the smoke suction regulator is selectively controllable by controller circuitry in the gas recirculation system. The controller circuitry may be configured to choose between recirculating the gas within the closed system of input and output tubing of the recirculation path passing through a patient's peritoneum (and the gas removal filters included therein), and suction exhaust tubing that connects with a suction source via the smoke suction valve that will quickly remove the gas and smoke if the smoke density rises faster than the closed recirculation path can adequately remove. Any of a number of known suction sources, including standalone pumps or built-in wall-mounted suction ports in medical facilities may be used as the suction source.

The suction source may be fixed at a predetermined flow rate or adjustable to any of a number of flow rates. In one implementation, the suction source may be capable of a minimum flow rate of 10 liters per minute (lpm). In some implementations, a minimum flow rate of 15 lpm for the suction source is contemplated to provide a faster flow than supported by the pump of the closed recirculation path when the smoke accumulation is too fast for the pump to handle on its own. In implementations when the suction source is a fixed flow rate source, the suction source may be always on, or controlled to be at either an on or off state by the controller. The smoke suction flow regulator 100 may be adjusted by the physician or medical staff during a procedure to adjust the suction flow rate applied to the recirculating gas being removed in implementations where the suction source is either always on or is only controllable between on and off states. In other implementations, the suction source may be a variable flow rate suction source adjustable by the controller circuitry. One aspect of the embodiments disclosed above is the variation in the flow settings allowed by the valve, for example being able to vary flow through the smoke suction regulator when a consistent negative pressure (e.g., vacuum source) is in use with it. The complementary threaded regions of the knob assembly 108 and the base 102 permit gradual closing or opening of the gas path 104 through the base 102 by the blocking portion on the end of the knob assembly 108 such that adjustment to any of a number of different flow rates may be achieved and maintained between a maximum flow level (fully open) and a minimum flow level (fully blocked).

A smoke evacuation regulator has been described that allows for variable and gradual flow through the use of a specific thread pitch and size, with a consistent and high negative pressure. A user may adjust the setting more confidently and consistently the user through external ridges and an indicator on the smoke evacuation assembly and a retention/snap feature to permanently lock the threaded knob into the base while allowing for variable flow settings has also been described. Although not shown, the use of a filter directly embedded into the flow-control valve for added filtration in the device may be used with any various applications, rather than using an inline filter that requires a specific assembly.

The invention claimed is:

1. A smoke evacuation regulator for use in managing removal of smoke from a flow of gas during an endoscopic surgical procedure, the smoke evacuation regulator comprising:
a body portion having a gas pathway extending from a first end to a second end of the body;
a knob assembly comprising:
a head positioned at a first end of the knob assembly, the head sized to receive an adjustment force from a user of the smoke evacuation regulator and having tactile indicia arranged on an outer surface identifiable by user touch to indicate a plurality of unique positions of the head corresponding to an amount the gas pathway is obstructed;
a gas pathway blocking extension positioned coaxially with, and extending away from, the head positioned at the first end of the knob assembly; and
a knob assembly protrusion extending radially away from an axis of the gas pathway blocking extension and positioned between the head and a distal end of the gas pathway blocking extension;
and
wherein the body portion defines a knob assembly receiving region extending through the gas pathway and positioned between the first and second ends of the body, the knob assembly receiving region comprising:
a position adjustment portion for receiving the knob assembly and permitting movement of the knob assembly through a predetermined range of positions in the body portion, wherein the position adjustment portion and the knob assembly cooperate to move the gas pathway blocking extension between a completely closed position and a completely open position in response to the adjustment force from the user; and
a retaining arm connected to the body portion and sized to limit a perpendicular movement of the knob assembly relative to the body.

2. The smoke evacuation regulator of claim 1, wherein the knob assembly protrusion comprises an annular surface facing, and parallel to, the head of the knob assembly and oriented coaxially with an longitudinal axis of the gas pathway blocking extension.

3. The smoke evacuation regulator of claim 1, wherein a side of the head opposite of the knob assembly protrusion is formed with a helical surface along a perimeter of the side of the head.

4. The smoke evacuation regulator of claim 3, wherein position indicators are positioned on the helical surface.

5. The smoke evacuation regulator of claim 4, wherein the body portion comprises a flow setting indicator fixedly positioned on, and extending from, the body portion such that the flow setting indicator is visible adjacent the head of the knob assembly.

6. The smoke evacuation regulator of claim 4, wherein the retaining arm comprises a first end attached to the body portion and a second end defining a barb sized to contact and prevent further movement of the knob assembly away from the body portion when the knob assembly is in a predetermined position relative to the body portion.

7. The smoke evacuation regulator of claim 1, wherein the gas pathway of the body portion comprises a tube having first and second ends, each of the first and second ends defining a circumferential barb sized to receive an end of flexible tubing.

8. The smoke evacuation regulator of claim 7, wherein each of the first and second ends of the gas pathway define an opening sized to transmit a flow of gas of at least 10 liters per minute under approximately 480 mmHG vacuum pressure.

9. A smoke evacuation regulator for use in managing removal of smoke from a flow of gas during an endoscopic surgical procedure, the smoke evacuation regulator comprising:
   a body portion having a gas pathway extending from a first end to a second end of the body;
   a knob assembly comprising:
      a head positioned at a first end of the knob assembly, the head sized to receive a rotational force from a user of the smoke evacuation regulator and having tactile indicia arranged on an outer surface identifiable by user touch to indicate a plurality of unique rotational positions of the head;
      a gas pathway blocking extension positioned coaxially with, and extending away from, the head positioned at the first end of the knob assembly; and
      a knob assembly protrusion extending radially away from an axis of the gas pathway blocking extension and positioned between the head and a distal end of the gas pathway blocking extension; and
   wherein the body portion defines a knob assembly receiving region extending through the gas pathway and positioned between the first and second ends of the body, the knob assembly receiving region comprising:
      a threaded portion for receiving a complementary threaded portion on the knob assembly, wherein the threaded portion and the complementary threaded portion cooperate to move the gas pathway blocking extension from a completely closed position to a completely open position over a single revolution of the knob assembly relative to the body; and
      a retaining arm connected to the body portion and sized to limit a perpendicular movement of the knob assembly relative to the body.

10. The smoke evacuation regulator of claim 9, wherein the knob assembly protrusion comprises an annular surface facing, and parallel to, the head of the knob assembly and having an axis of rotation oriented coaxially with the axis of the gas pathway blocking extension.

11. The smoke evacuation regulator of claim 9, wherein a side of the head opposite of the knob assembly protrusion is formed with a helical surface along a perimeter of the side of the head.

12. The smoke evacuation regulator of claim 11, wherein rotational position indicators are positioned on the helical surface.

13. The smoke evacuation regulator of claim 12, wherein the body portion comprises a flow setting indicator fixedly positioned on, and extending from, the body portion such that the flow setting indicator is visible adjacent an outer diameter of the head of the knob assembly.

14. The smoke evacuation regulator of claim 12, wherein the retaining arm comprises a first end attached to the body portion and a second end defining a barb sized to contact and prevent further movement of the knob assembly away from the body portion when the knob assembly is in a predetermined maximum unthreaded position relative to the body portion.

15. The smoke evacuation regulator of claim 9, wherein the gas pathway of the body portion comprises a tube having first and second ends, each of the first and second ends defining a circumferential barb sized to receive an end of flexible tubing.

16. The smoke evacuation regulator of claim 15, wherein each of the first and second ends of the gas pathway define an opening sized to transmit a flow of gas of at least 10 liters per minute under approximately 480 mmHG vacuum pressure.

17. A smoke evacuation regulator for use in managing removal of smoke from a flow of gas during an endoscopic surgical procedure, the smoke evacuation regulator comprising:
   a body portion having a gas pathway extending from a first end to a second end of the body; and
   a gas flow adjuster movably positioned on the body portion, the gas flow adjuster being adjustable to a plurality of positions relative to the body portion to controllably set a gas flow via the gas flow path;
   wherein the gas flow adjuster further comprises:
      a head positioned at a first end of the gas flow adjuster, the head sized to receive a force from a user of the smoke evacuation regulator and having tactile indicia arranged on an outer surface identifiable by user touch to indicate a plurality of unique positions of the gas flow adjuster relative to the body portion; and
      a gas pathway blocking extension positioned coaxially with, and extending away from, the head positioned at the first end of the gas flow adjuster; and
      a travel limiter extension positioned along the gas flow adjuster; and
   wherein the body portion defines a gas flow control opening in the gas pathway between the first and second ends of the body, the gas flow control opening sized to receive the gas pathway blocking extension; and
   wherein the body portion further comprises a flexible travel limiter arm positioned on an exterior of the body portion, the flexible travel limiter arm movable to permit assembly of the body portion and the gas flow adjuster, and positioned to contact the travel limiter extension to limit a range of movement of the gas flow adjuster relative to the body portion and to prevent disassembly of the gas flow adjuster from the body portion during operation of the smoke evacuation regulator.

18. The smoke evacuation regulator of claim 17, wherein the gas flow regulator is rotatably adjustable relative to the body portion and wherein the tactile indicia arranged on the outer surface of the head of the gas flow adjuster are sets of different number ridges spaced around a circumference of the head.

19. The smoke evacuation regulator of claim 18, wherein a top surface of the head of the gas flow adjuster forms a helical surface.

20. The smoke evacuation regulator of claim 19, wherein the gas flow adjuster is movable relative to the body portion to adjust a flow of gas through the gas flow path between a maximum open position and a fully closed position via a single revolution of the gas flow adjuster.

\* \* \* \* \*